(12) United States Patent
Pack et al.

(10) Patent No.: US 6,692,911 B2
(45) Date of Patent: *Feb. 17, 2004

(54) CELL DELIVERY COMPOSITIONS

(75) Inventors: Daniel W. Pack, Champaign, IL (US); David A. Putnam, Cambridge, MA (US); Robert S. Langer, Newton, MA (US)

(73) Assignee: Massachusetts Institute of Technology

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 285 days.

(21) Appl. No.: 09/251,783

(22) Filed: Feb. 17, 1999

(65) Prior Publication Data

US 2001/0006817 A1 Jul. 5, 2001

Related U.S. Application Data

(60) Provisional application No. 60/075,272, filed on Feb. 19, 1998.

(51) Int. Cl.$^7$ .......................... C12Q 1/68; C12P 21/66; C12N 15/00; C12N 15/63; C12N 15/86
(52) U.S. Cl. ..................... 435/6; 435/69.1; 435/91.1; 435/440; 435/455; 435/456; 435/458; 435/325; 424/450
(58) Field of Search ............................ 424/450; 435/6, 435/69.1, 91.1, 440, 455, 456, 458, 325; 530/300; 536/23.1; 514/44

(56) References Cited

U.S. PATENT DOCUMENTS

| | | | |
|---|---|---|---|
| 4,104,466 A | | 8/1978 | Tsuchida et al. ............... 546/2 |
| 5,583,020 A | * | 12/1996 | Sullivan ................... 435/172.3 |
| 5,908,777 A | * | 6/1999 | Lee et al. ................. 435/320.1 |
| 5,912,239 A | * | 6/1999 | Siegel et al. ................. 514/182 |
| 5,965,434 A | * | 10/1999 | Wolff et al. .............. 435/320.1 |
| 6,033,884 A | * | 3/2000 | Woo et al. | 
| 2001/0007666 A1 | * | 7/2001 | Hoffman et al. |

FOREIGN PATENT DOCUMENTS

| | | |
|---|---|---|
| WO | WO 95/02397 | 1/1995 |
| WO | WO 96/11712 | 4/1996 |
| WO | WO 96/21036 | 7/1996 |
| WO | WO 96/22792 | 8/1996 |
| WO | WO 96/41606 | 12/1996 |
| WO | WO 97/07226 | 2/1997 |
| WO | WO 97/10851 | 3/1997 |
| WO | WO 98/28626 | 7/1998 |

OTHER PUBLICATIONS

Liang, E. et al. Pharmaceutical Research, vol. 12 (9 Suppl.): p. S241, Sep. 1995.*
Lasic, D.D. Journal of Controlled Release, vol. 48, pp. 203–222, 1997.*
Marc Lemaitre et al., Specific Antiviral Activity of a Poly(L–Lysine)–Conjugated Oligodeoxyribonucleotide Sequence Complementary to Vesicular Stomatitis Virus N Protein Mrna Initiation Site; Proc. Natl. Acad. Sci. USA, Feb. 1987, vol. 84, pp. 648–652.*
Patrick Midoux et al., Specific Gene Transfer Mediated by Lactosylated Poly–L–Lysine into Hepatoma Cells; Nucleic Acids Research, 1993, vol. 21, No. 4 pp. 871–878.*
Ernst Wagner et al., Transferrin–Polycation–DNA Complexes: the Effect of Polycations on the Structure of the Complex and DNA Delivery to Cells; Proc. Natl. Acad. Sci. USA 88 May 1991, pp. 4255–4259.*
Abdallah et al., "Non–Viral Gene Transfer: Applications in Developmental Biology and Gene Therapy" *Biol. Cell*, 85:1–7, 1995.
Boussif et al., "A Versatile Vector for Gene and Oligonucleotide Transfer into Cells in Culture and In Vivo: Polyethylenimine" *Proc. Natl. Acad. Sci. USA* 92(16):7297–7301, Aug. 1995.
Cotten et al., "Chicken Adenovirus (CELO virus) Particles Augment Receptor–Mediated DNA Delivery to Mammalian Cells and Yield Exceptional Levels of Stable Transformants" *J. Virol.* 67(7):3777–3785, Jul. 1993.
Cotten et al., "Receptor–Mediated Transport of DNA into Eukaryotic Cells" *Methods Enz.*, 217:618644, 1993.
Gottschalk et al., "Synthetic Vehicles for Efficient Gene Transfer and Expression in Mammalian Cells (Meeting abstract)" *J. Cell Biochem.* (Suppl. 21A)393, 1995.
Hagmann et al., "Release of Endosomal Content Induced by Plasma Membrane Tension: Video Image Intensification Time Lapse Analysis" *Exp. Cell Res.* 198:298–304, 1992.

(List continued on next page.)

*Primary Examiner*—Karen Lacourciere
(74) *Attorney, Agent, or Firm*—Choate, Hall & Stewart; Brenda H. Jarrell; C. Hunter Baker

(57) ABSTRACT

The present invention provides improved cell delivery compositions. In particular, the invention provides biocompatible endosomolytic agents. In a preferred embodiment, the endosomolytic agents are also biodegradable and can be broken down within cells into components that the cells can either reuse or dispose of. Preferred endosomolytic agents include cationic polymers, particularly those comprised of biomolecules, such as histidine, polyhistidine, polylysine or any combination thereof. Other exemplary endosomolytic agents include, but are not limited to, other imidazole containing compounds such as vinylimidazole and histamine. More particularly preferred are those agents having multiple proton acceptor sites and acting as a "proton sponge", disrupting the endosome by osmolytic action. In preferred embodiments, the endosomolytic agent comprises a plurality of proton acceptor sites having pKas within the range of 4 to 7, which endosomal lysing component is polycationic at pH 4. The present invention also contemplates the use of these endosomolytic agents as delivery agents by complexation with the desired compound to be delivered. Thus, the present invention also acts as a cell delivery system comprising an endosomolytic agent, a delivery agent, and a compound to be delivered.

39 Claims, 15 Drawing Sheets

OTHER PUBLICATIONS

Harris, "Gene Delivery and Therapy Strategies" *The Lancet*, 342:234, Jul. 24, 1993.

Harris et al., "Receptor–Mediated Gene Transfer to Airway Epithelial Cells in Primary Culture" *Am. J. Respir. Cell Mol. Biol.* 9(4):441–447, 1993.

Hui et al., "The Role of Helper Lipids in Cationic Liposome–Mediated Gene Transfer" *Biophys. J.* 71:590–599, Aug. 1996.

Kabanov et al., "DNA Complexes with Polycations for the Delivery of Genetic Material into Cells" *Bioconjugate Chemistry* 6(1):7–20, 1995.

Kornguth et al., "Effects of Polylysine on the Leakage and Retention of Compounds by Ehrlich Ascites Tumor Cells" *Cancer Research* 21:907–912, Aug. 1961.

Plank et al., "The Influence of Endosome–Disruptive Peptides on Gene Transfer Using Synthetic Virus–Like Gene Transfer Systems" *J. Biol. Chem.* 269(17):12918–12924, Apr. 29, 1994.

Schwarzenberger et al., "Receptor–Targeted Recombinant Adenovirus Conglomerates: A Novel Molecular Conjugage Vector with Improved Expression Characteristics" *J. Virol.* 71(11):8563–8571, Nov. 1997.

Wagner et al., "Transferrin–Polycation Conjugates as Carriers for DNA Uptake Into Cells" *Proc. Natl. Acad. Sci. USA*, 87:3410–3414, May 1990.

Wagner et al., "Influenza Virus Hemagglutinin HA–2 N–Terminal Fusogenic Peptides Augment Gene Transfer by Transferrin–Polylysine–DNA Complexes: Toward a Synthetic Virus–Like Gene–Transfer Vehicle" *Proc. Natl. Acad. Sci. USA* 89:7934–7938, Sep. 1992.

Wagner, "Receptor–mediated gene transfer: the answer in tumor immunotherapy?" *Molekularbiol. Grundlagen Gastroenterol.* (Beger et al., eds.) Berlin:Springer Verlag, 389–392, 1995.

Wagner et al., "Receptor–Mediated Delivery of Plasmid DNA" *Biogenic Amines* 14(5):519–536, 1998.

Zatloukal et al., "Transferrinfection: A Highly Efficient Way to Express Gene Constructs in Eukaryotic Cells" *Ann. N. Y. Acad. Sci.* 660:136–53, 1992.

Zauner et al., "Glycerol and Polylysine Synergize in their Ability to Rupture Vesicular Membranes: A Mechanism for Increased Transferrin–Polylysine–Medicated Gene Transfer" *Exp. Cell Res.* 232:137–145, 1997.

Zauner et al., "Polylysine–Based Transfection Systems Utilizing Receptor–Mediated Delivery" *Adv. Drug Delivery Rev.* 30:97–113, 1998.

Zenke et al., "Receptor–Mediated Endocytosis of Transferrin–Polycation Conjugates: An Efficient Way to Introduce DNA into Hematopoietic Cells" *Proc. Natl. Acad. Sci. USA* 87:3655–3659, May 1990.

* cited by examiner

Poly(histidine) may function as a biopolymeric proton-sponge.

Copolymer of Polylysine and Histidine

Copolymer of Polylysine and Polyhistidine

DNA/G-pHis/Tfpk complexes transfect approximately 10% of COS-7 cells

X-gal staining of COS-7 cells 48 h post-transfection:

A. DNA only:     no blue cells
B. DNA/G-pHis/Tfpk:  ~10%
   (1:3:4.5)
C. LipofectAMINE:   ~45%

CELL DELIVERY COMPOSITIONS

PRIORITY INFORMATION

This application claims priority to the co-pending provisional application No. 60/075,272 entitled "Cell Delivery Compositions" filed on Feb. 19, 1998, which is incorporated in its entirety by reference.

GOVERNMENT SUPPORT

The present research was supported by a grant from the National Institutes of Health (Grant Number GM26698).

BACKGROUND OF THE INVENTION

The recent revolutions in molecular and pharmaceutical biology and pharmaceutical chemistry have created a need for the development of effective mechanisms for delivering biological and other therapeutic agents into cells. Researchers have particularly struggled to develop an efficient means of introducing nucleic acids into cells, for example for gene therapy, antisense therapy, or research purposes (e.g., to study cell differentiation, growth and carcinogenic transformation or to create animal models for human disease; see, for example, Abdallah, *Biol. Cell,* 85:1, 1995 and references therein).

Unfortunately, existing techniques for delivering nucleic acids to cells are limited by poor efficiency and/or high toxicity of the delivery reagents. A particular problem is encountered with techniques that rely on receptor-mediated endocytosis (see, e.g., FIG. 1) because the nucleic acid to be delivered is often destroyed when exposed to the low pH and active degradatory machinery of the endosome/lysosome. Various reagents (e.g., chloroquine, polyethylenimine [PEI], certain highly charged cationic compounds, fusogenic peptides, and inactivated adenoviruses) have been developed that are intended to quickly disrupt the endosome in order to minimize the amount of time that a delivered nucleic acid spends in this hostile environment.

Certain of these known compounds (i.e., chloroquine, PEI), are thought to act as so-called "proton-sponges" because they contain a large number of proton-acceptor sites. It is thought that these compounds sop up protons in the endosome, thereby increasing the pH in the endosome (see, for example, Boussif et al., *PNAS,* 92:7297, 1995). This pH increase both inhibits the action of lysosomal nucleases with acid-optimal pH dependence and induces an ATPase proton pump in the endosomal membrane to furiously pump additional protons from the cytoplasm into the endosome in order to restore the proper endosomal pH. Because the ATPase pump carries one chloride ion into the endosome with every proton that it transfers from the cytoplasm, its excessive pumping creates an osmotic pressure imbalance that results in lysis of the endosome (see Behr, ILMAC, 1st Swiss Cost Chemistry Symposium, 1996; see also FIG. 2).

The highly charged cationic compounds are thought to burst open the endosomal compartment by a different mechanism that involves fusing with and lysing open the bilayer membranes. The fusogenic peptides and inactivated viruses rely on viral lysis capabilities to burst the endosome compartment.

Although these known endosomolytic agents do appear to increase the efficiency of nucleic acid delivery, they have serious toxicity problems and other disadvantages. Some (e.g., chloroquine) are simply poisonous to cells. Others (e.g., viral compounds) can activate the immune system, thereby risking systemic difficulties and also creating the possibility that the host immune system will destroy the agent relied upon to effect cell delivery. There remains a need for the development of a biocompatible, preferably biodegradable, endosomolytic cell delivery agent. There is a particular need for an agent that can efficiently introduce nucleic acids into cells.

SUMMARY OF THE INVENTION

The present invention provides improved cell delivery compositions. In particular, the invention provides a biocompatible endosomolytic system. These inventive endosomolytic agents obviate the need for known agents (i.e., chloroquine, fusogenic peptides, inactivated adenoviruses, and polyethyleneimine) that can burst endosomes but have negative effects on cells. Preferred inventive endosomolytic agents are biodegradable in that they are broken down within cells into components that the cells can either reuse or dispose of. Particularly preferred inventive endosomolytic agents are cationic polymers comprised of biomolecules. Although the present invention is not limited by the mechanism of action of the endosomolytic agents, certain preferred agents have multiple proton acceptor sites and would be expected to act as "proton sponges", disrupting the endosome by osmolytic action. Particularly preferred agents are polycationic under the conditions of the endosome (i.e., at pH 4). Exemplary endosomolytic agents include, but are not limited to, imidazole containing compounds such as histidine, histamine, vinylimidazole, polymers thereof, and any combinations thereof.

In one preferred embodiment of the invention, the endosomolytic agent comprises polyhistidine. Polyhistidine for use in accordance with the present invention may be provided as a linear or branched polyhistidine polymer. Moreover, as is discussed further below, the polyhistidine may be provided in combination with one or more additional agents. Where such other agents are other polymers, or functionalizable chemical compounds, they may be co-polymerized or functionalized with polyhistidine or histidine. Thus, a polyhistidine endosomolytic agent of the present invention need not comprise a polyhistidine polymer per se, so long as it has a sufficient number of histidine functional groups to preserve poyhistidine functionality as described herein. To give but one example, the inventive endosomolytic agent may comprise a single linear or branched copolymer synthesized from any appropriate combination of polyhistidine, polylysine, histidine, and/or lysine.

The endosomolytic agents of the present invention may be employed in any of a variety of delivery contexts. In some cases, the endosomolytic agent also acts as a delivery agent; in other cases, the endosomolytic agent is combined with a delivery agent that complexes the compound being delivered in a manner that allows that compound to be taken into an endosome and thereby introduced into a cell. Thus, the present invention also provides a cell delivery system comprising an endosomolytic agent, a delivery agent, and a compound to be delivered. In preferred embodiments, the compound to be delivered comprises nucleic acid. Also, certain preferred cell delivery systems include a targeting agent, preferably covalently linked to one or more of the endosomolytic agent, the delivery agent, and the delivery compound.

In one particularly preferred embodiment of the cell delivery system of the present invention, the endosomolytic agent comprises or consists of polyhistidine, the delivery agent comprises or consists of polylysine, and the delivery compound comprises or consists of nucleic acid, preferably DNA. The polyhistidine and polylysine may be mixed together as separate components or may be formulated together as a single linear or branched copolymer. That is, any appropriate combination of polyhistidine and polylysine, polyhistidine and lysine, or histidine and polylysine may be employed in accordance with the present invention.

DEFINITIONS

"Biocompatible"—The term "biocompatible", as used herein is intended to describe compounds that are not toxic to cells. Compounds are "biocompatible" if their addition to cells in vitro results in less than or equal to 20% cell death and do not induce inflammation or other such adverse effects in vivo.

"Biodegradable"—As used herein, "biodegradable" compounds are those that, when introduced into cells, are broken down by the cellular machinery into components that the cells can either reuse or dispose of without significant toxic effect on the cells (i.e., fewer than about 20% of the cells are killed).

"Biomolecules"—The term "biomolecules", as used herein, refers to molecules (e.g., proteins, amino acids, nucleic acids, nucleotides, carbohydrates, sugars, lipids, etc.) that are found in living cells in nature.

"Known endosomolytic agents"—The phrase "known endosomolytic agents", as used herein, refers to a particular set of compounds: chloroquine, fusogenic peptides, inactivated adenoviruses, and polyethyleneimine, that were known on the day the present application was filed to have osmolytic capabilities. The classification of such compounds as "known" is not intended to represent that such compounds constitute prior art to the present invention, nor is it intended to represent that the osmolytic capability of the agent was known prior to the date of the present invention.

"Proton sponge"—The term "proton sponge", as used herein, refers to a compound with a sufficient number of proton acceptor sites that, when the compound is introduced into an endosome within a living cell, endosomal protons associate with the compound so that the endosomal pH rises, the endosomal proton pump is activated to transfer protons and counter ions into the endosome, and the osmotic pressure within the endosome rises to a point that bursts the endosome. "Proton sponge" is used interchangeably with "osmolytic agent" herein.

DESCRIPTION OF THE DRAWING

FIG. 5A shows a copolymer of polylysine and histidine. FIG. 5B shows a copolymer of polylysine and polyhistidine.

DETAILED DESCRIPTION OF THE PREFERRED EMBODIMENTS

In recognition of the importance of the development of a safe and effective cell delivery system, the present invention provides improved compositions and methods for the delivery of therapeutic agents to cells and subcellular components. In one aspect, the present invention provides a biocompatible endosomolytic system. These inventive endosomolytic agents obviate the need for known agents (i.e., chloroquine, fusogenic peptides, inactivated adenoviruses, and polyethyleneimine) that can burst endosomes but have negative effects on cells. In another aspect, the present invention provides a cell delivery system comprising an inventive endosomolytic agent, and a delivery agent. Certain examples of preferred endosomolytic systems and cell delivery systems are presented below.

Endosomolytic Agents

As discussed above, the present invention provides an improved system for delivery of compounds to cells and lysis of endosomal cell compartments. In particular, the invention provides biocompatible, preferably biodegradable, endosomolytic agents. While the mechanism of action of the endosomolytic agents is not intended to limit the scope of the present invention, preferred agents have multiple proton acceptor sites (i.e., multiple groups with a pKa intermediate between pH 4 and pH 7) and/or are polycationic, at least when they are within the endosome. Particularly preferred agents are linear or branched polymers of biomolecules, preferably of amino acids or amino acid derivatives. Exemplary endosomolytic agents include, but are not limited to, imidazole containing compounds such as histidine, histamine, vinylimidazole, polymers thereof, and any combinations thereof.

As one of ordinary skill in the art will realize, the endosomolytic agents of the present invention must be of appropriate size to fit inside an endosomal compartment, along with any agent to be delivered to the cell. Inventive agents are therefore less than about 150 nm in size, or are capable of adopting a conformation less that about 150 nm in size for purposes of uptake via endocytosis.

Figure 1:
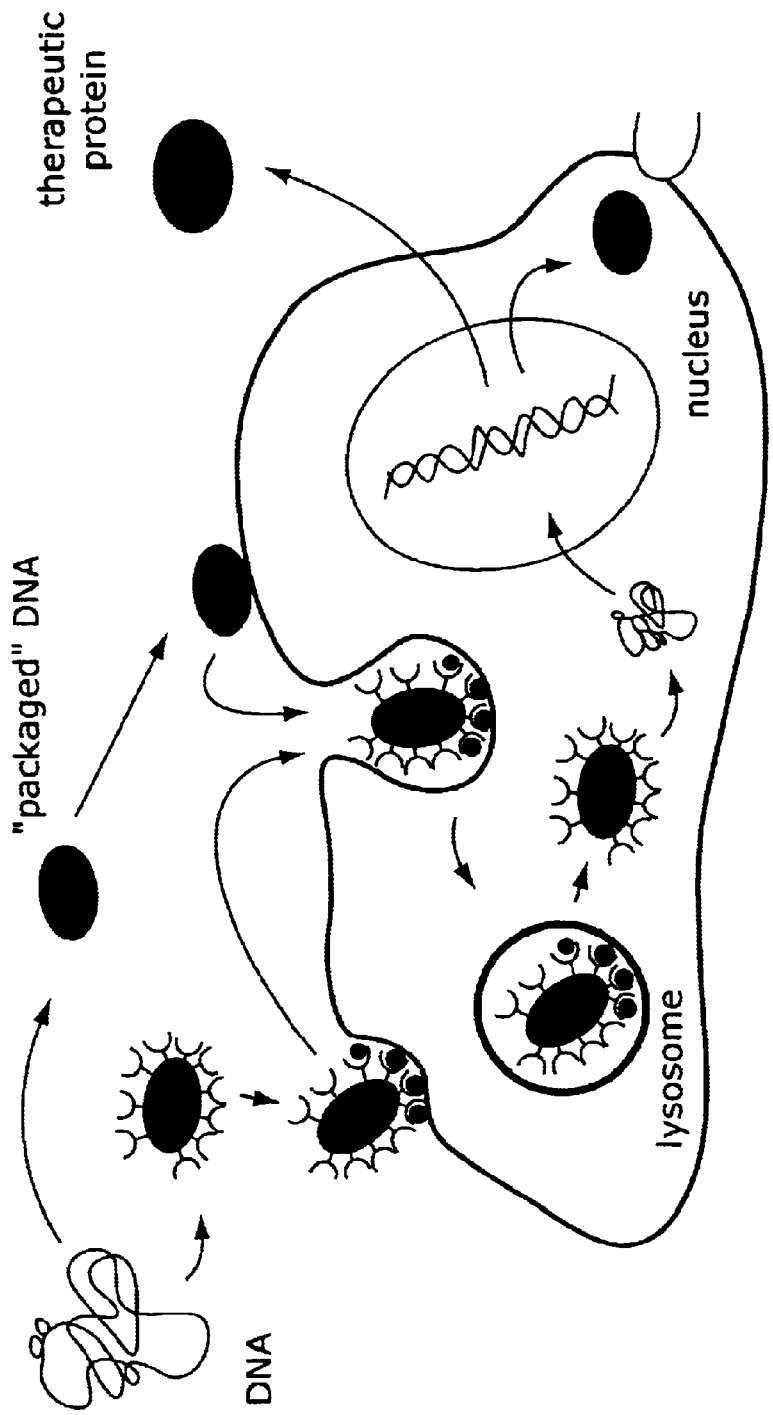
FIG. 1 diagrams delivery of DNA into a cell cytoplasm by receptor mediated endocytosis.
Figure 2:
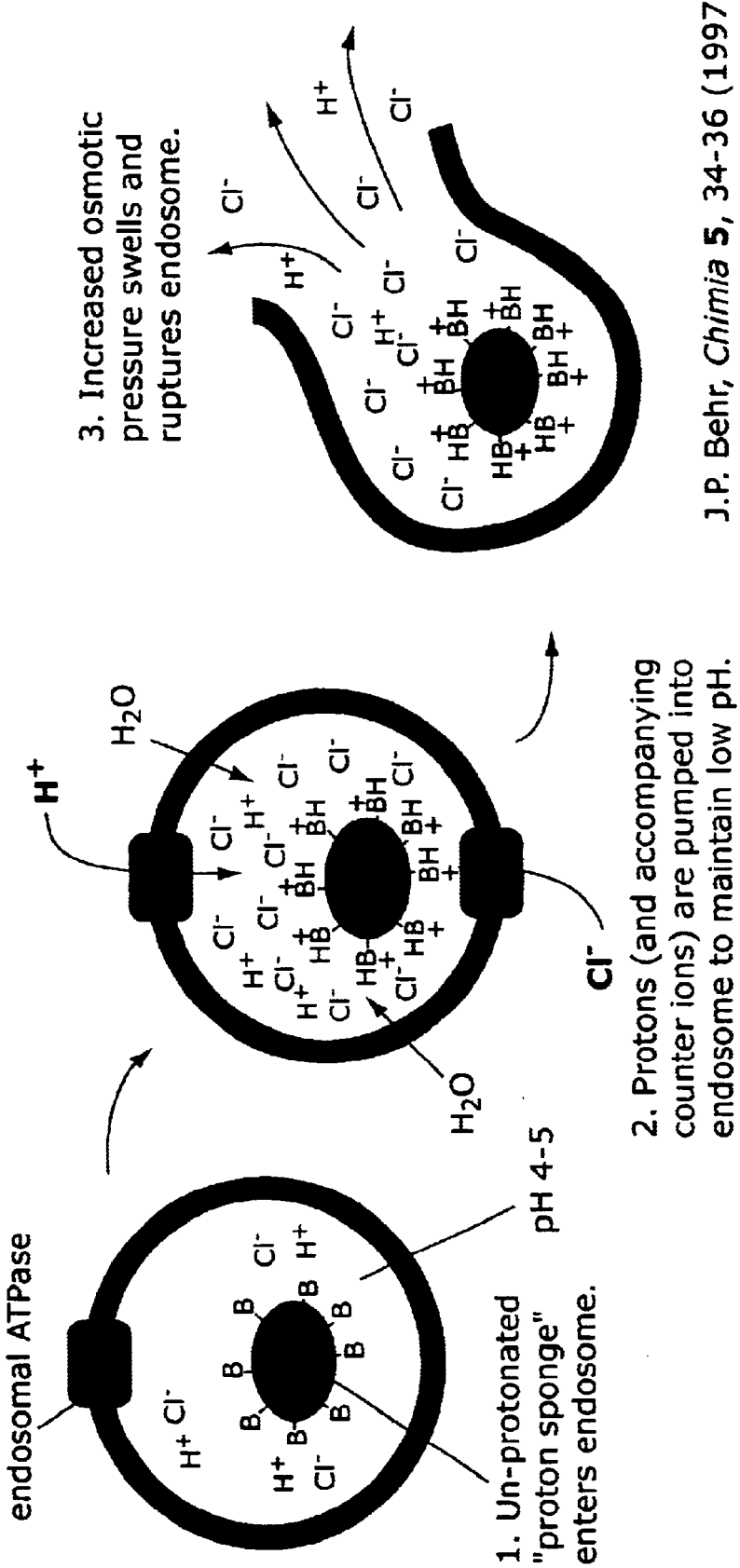
FIG. 2 depicts the process by which "proton-sponge" polymers are believed to mediate release of delivered compounds (e.g., DNA) from lysosomes.
Figure 3:
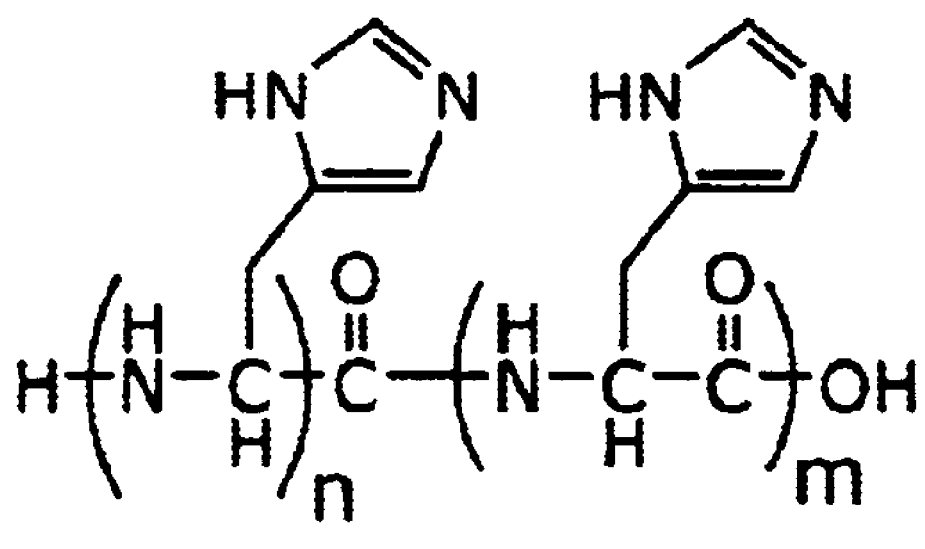
FIG. 3 depicts of the chemical structure of polyhistidine.
Figure 4:
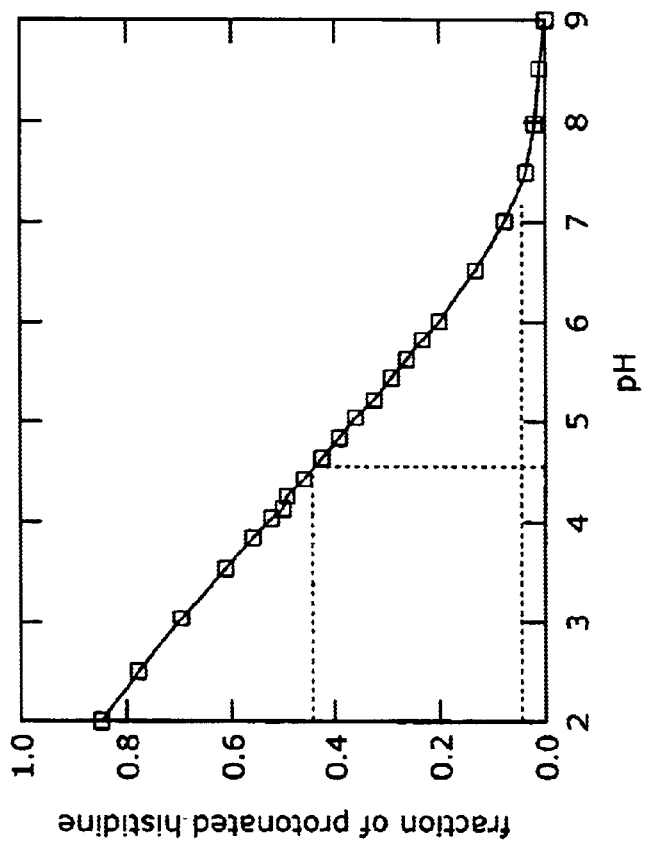
FIG. 4 shows the chemical structure of polyhistidine and its protonation as a function of pH demonstrating that polyhistidine functions as a biopolymeric proton sponge.
Figure 4:
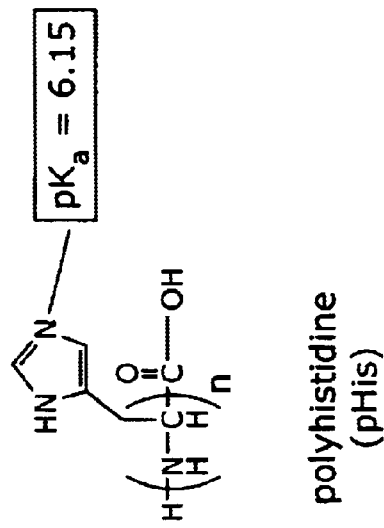

Polyhistidine (FIG. 3) is one example of a particularly preferred endosomolytic agent of the present invention. The histidine imidazole side chain has a pKa of 6.5, so that polyhistidine has multiple proton acceptor sites according to the present invention. Polyhistidine is protonated, and therefore polycationic, at pH 4 (i.e., within the endosome). As shown in FIG. 4, polyhistidine is expected to act as a proton sponge in endosomes; the present invention is not limited to such a mechanism, however.

The polyhistidine endosomolytic agent of the present invention may be a linear polymer or a branched polymer. Moreover, the polyhistidine may be combined or polymerized with one or more additional agents with desirable cell delivery attributes. For example, the polyhistidine may be combined with a delivery agent selected to interact with the compound to be delivered to the cell. However, the polyhistidine of the present invention is not combined with chloroquine, fusogenic peptides, inactivated adenoviruses, and polyethyleneimine.

In another particularly preferred embodiment of the present invention, polyhistidine is combined with polylysine to deliver nucleic acid to cells. Polylysine is known to bind to nucleic acids and to compact them (Cotten et al., *Methods Enz.*, 217: 644, 1993). Thus, polylysine is a useful delivery agent for nucleic acids. In fact, prior to the present invention, efforts had been made to use polylysine for delivery of nucleic acids to cells (see, for example, Wagner et al., *PNAS*, 87: 3410, 1990). However, polylysine-mediated delivery was inefficient in the absence of an endosomolytic agent, and known endosomolytic agents were toxic. The present invention remedies this difficulty.

Figure 5A:
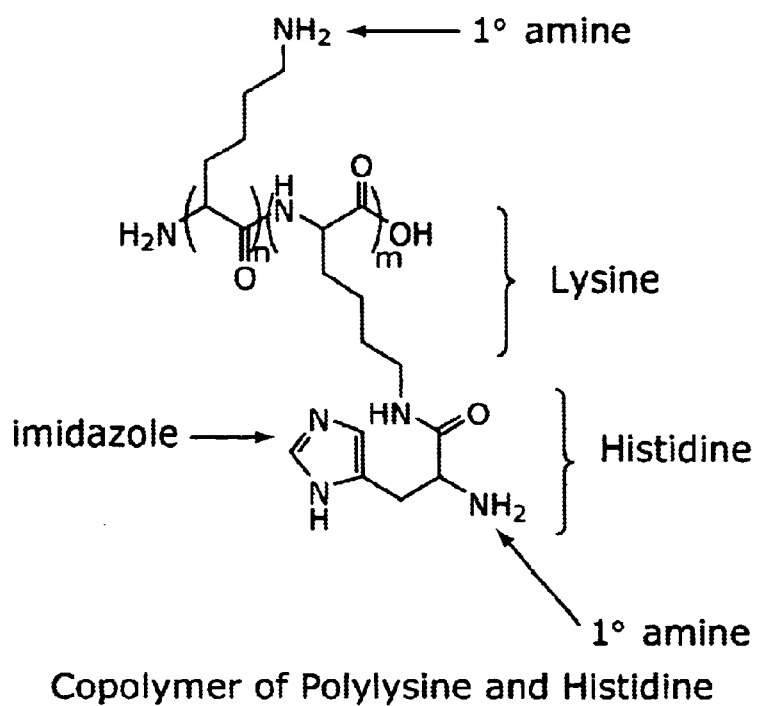
FIGS. 5A and 5B depict certain preferred cell delivery compositions of the present invention. In particular.
Figure 5B:
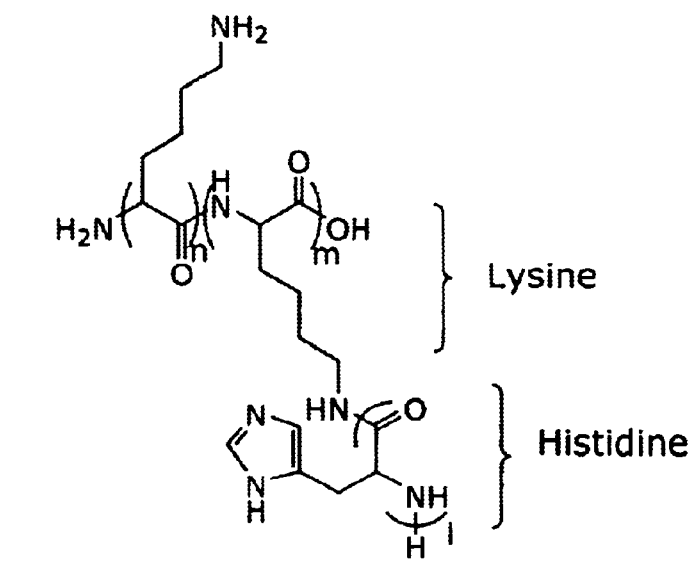

FIGS. 5A and 5B depict certain polyhistidine and polyhistidine/polylysine compositions of the present invention. Polyhistidine and polylysine can be prepared (or purchased) separately and combined together in various ratios; or can be covalently linked to one another in linear or branched co-polymers of any form (e.g., graft co-polymers, dendritic co-polymers, etc.). Moreover, histidine and lysine may be "polymerized together", such that the product polymer contains histidine and lysine units in any desirable arrangement.

Those of ordinary skill in the art will, using known techniques, be able to prepare any of a variety of polyhistidine/polylysine compositions that can readily be tested according to the teachings herein to identify those with desirable delivery characteristics. The compositions must have sufficient polyhistidine composition (including available proton acceptor sites and/or polycationic character) to lyse endosomes, and sufficient polylysine composition to bind to nucleic acids, and condense them if necessary. Thus, the inventive polyhistidine/polylysine composition may comprise any combination of polylysine with polyhistidine, polylysine with histidine, or lysine with polyhistidine, associated with one another covalently or otherwise, so long as the combination is biocompatible and has the endosomolytic and nucleic acid binding/packaging capabilities described herein. As one of ordinary skill in the art will realize, the entire composition (including the bound nucleic acid) must be small enough to be taken up into cells. As mentioned above, endosomal compartments can usually accept entities up to about 150 nm in size.

In addition, or as an alternative to being combined with a delivery agent, the endosomolytic agent of the present invention may be combined with one or more other agents to achieve, for example, a desired solubility or targeting to a particular cell or cell type. Cell targeting is discussed in more detail below; solubility adjustments are readily accomplished, for example, by functionalizing the endosomolytic agent, or another factor with which it is associated, with a hydrophilic moiety. For example, the above-described polyhistidine endosomolytic agent of the present invention can be solubilized through functionalization with gluconic acid (see FIG. 6) or other moieties including but not limited to, carbohydrates, nucleic acids, and amino acids.

Delivery Agents

As one of ordinary skill in the art will realize, the selection of delivery agent for use in accordance with the present invention depends on the compound to be delivered. The delivery agent is thus any biocompatible (preferably biodegradable) entity that interacts with the compound to be delivered in such a way as to mediate its introduction into a cell.

For example, as discussed above, polylysine is a useful delivery agent for nucleic acids. Other nucleic acid delivery agents can readily be identified. For example, compounds with a high charge density are likely to be able to interact with, and often package, DNA. Preferred compounds are biopolymers (i.e., polymers of biomolecules) with at least one charge per monomer unit.

Those of ordinary skill in the art will recognize that inventive compositions comprising an endosomolytic agent, a nucleic acid delivery agent, and a nucleic acid are, in effect, artificial viruses characterized in being non-immunogenic, capable of circulation in the bloodstream, targetable to particular cells (i.e., when a targeting agent is employed) and less than 150 nM in size.

Targeting Agents

It is often desirable to target a cell delivery composition to a particular cell or collection of cells. A variety of agents that direct compositions to particular cells are known in the art (see, for example, Cotten et al., *Methods Enzym*, 217: 618, 1993). Preferred targeting agents are biocompounds, or portions thereof, that interact specifically with individual cells, small groups of cells, or large categories of cells. Examples of useful targeting agents include, but are in no way limited to, low-density lipoproteins (LDLs), transferrin, asiaglycoproteins, gp120 envelope protein of the human immunodeficiency virus (HIV), and diptheria toxin, antibodies, and carbohydrates.

Figure 7:
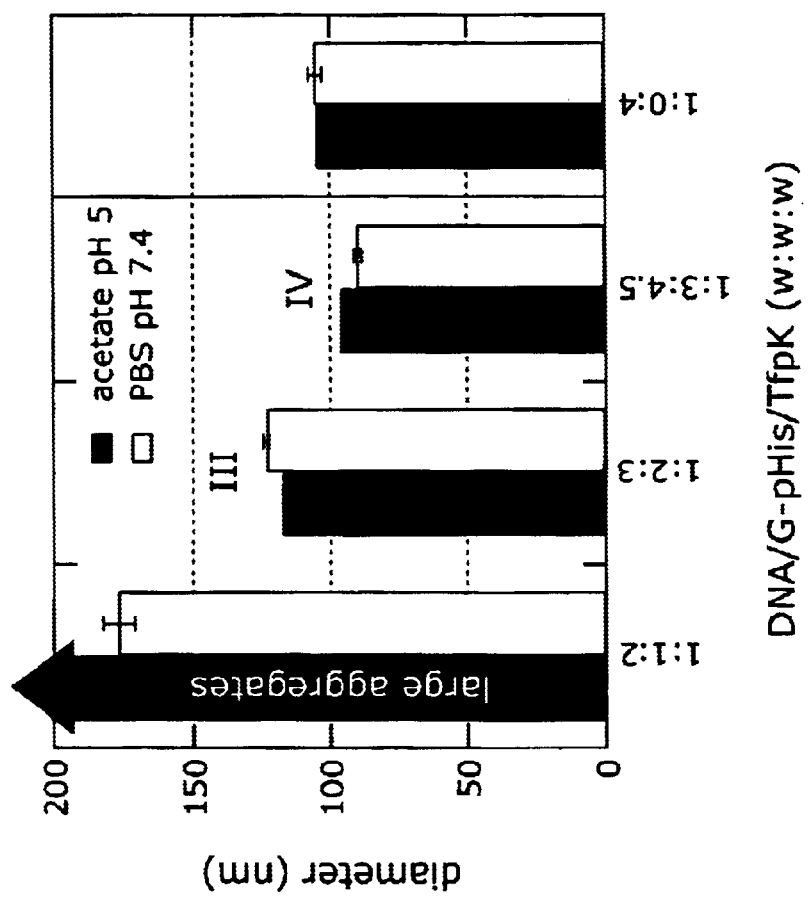
FIG. 7 is a graph demonstrating that DNA/gluconoyl-polyhistidine/transferrin-polylysine complexes are well below the size limit of 150 nm for endocytosis.

Certain preferred endosomolytic compositions of the present invention include one or more targeting agents associated with (e.g., by covalent, hydrophobic, hydrogen-bonding, van der Waals, or other interaction) the inventive endosomolytic agent, the delivery agent, and/or the delivery compound. To give but one example, Example 2 describes a polyhistidine/polylysine inventive composition in which at least some of the polylysine is covalently linked to transferrin. As shown in FIG. 7, this composition is less than 150 nm in size.

Delivery Compounds

In principle, any substance having biological activity may be delivered to cells using the endosomolytic and/or cell delivery systems of the present invention. For example, the invention includes but is not limited to delivery of proteins, polypeptides, polynucleotides, nucleoproteins, polysaccharides, glycoproteins, lipoproteins, and synthetic and biologically engineered analogs thereof.

Examples of biologically active compounds that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. §§330.5, 331 through 361; 440–460; drugs for veterinary use listed by the FDA under 21 C.F.R. §§500–582, incorporated herein by reference, are all considered acceptable for use in the present inventive cell delivery composition.

Biologically active compounds for use in the present invention include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human.

Classes of pharmaceutically active compounds that can be used in the practice of the present invention include, but are not limited to, anti-AIDS substances, anti-cancer substances, antibiotics, immunosuppressants (e.g., cyclosporine), anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, vaccines, ribozymes, anti-sense agents, and RNA.

A more complete listing of classes of compounds suitable for delivery into cells according to the present invention may be found in the Pharmazeutische Wirkstoffe (Von Kleemann et al. (eds) Stuttgart/New York, 1987, incorporated herein by reference). Examples of particular pharmaceutically active substances are presented below:

Anti-AIDS substances are substances used to treat or prevent Autoimmune Deficiency Syndrome (AIDS). Examples of such substances include, but are not limited to, CD4, 3'-azido-3'-deoxythymidine (AZT), 9-(2-hydroxyethoxymethyl)-guanine (acyclovir), phosphonoformic acid, 1-adamantanamine, peptide T, and 2',3' dideoxycytidine.

Anti-cancer substances are substances used to treat or prevent cancer. Examples of such substances include, but are not limited to, methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include, but are not limited to, penicillin, tetracycline, chloramphenicol, minocycline, doxycycline, vanomycin, bacitracin, kanamycin, neomycin, gentamycin, erythromicin and cephalosporins.

Anti-viral agents are substances capable of destroying or suppressing the replication of viruses. Examples of anti-viral agents include, but are not limited to, α-methyl-P-adamantane methylamine, 1,-D-ribofuranosyl-1,2,4-triazole-3 carboxamide, 9-[2-hydroxy-ethoxy] methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include, but are not limited to, edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N_6$-monomethyl-L-arginine acetate, carbidopa, 3-hydroxybenzylhydrazine HCl, hydralazine HCl, clorgyline HCl, deprenyl HCl,L(−)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate, S(−)-, 3-iodotyrosine, alpha-methyltyrosine, L-, alpha -methyltyrosine, D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include, but are not limited to, adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide.

Opioids are substances having opiate like effects that are not derived from opium. Opioids include opioid agonists and opioid antagonists. Opioid agonists include, but are not limited to, codeine sulfate, fentanyl citrate, hydrocodone bitartrate, loperamide HCl, morphine sulfate, noscapine, norcodeine, normorphine, thebaine. Opioid antagonists include, but are not limited to, nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include, but are not limited to, pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include, but are not limited to, pyrilamine, chlorpheniramine, tetrahydrazoline, and the like.

Lubricants are substances that increase the lubricity of the environment into which they are delivered. Examples of biologically active lubricants include, but are not limited to, water and saline.

Tranquilizers are substances which provide a tranquilizing effect. Examples of tranquilizers include, but are not limited to, chloropromazine, promazine, fluphenzaine, reserpine, deserpidine, and meprobamate.

Anti-convulsants are substances which have an effect of preventing, reducing, or eliminating convulsions. Examples of such agents include, but are not limited to, primidone, phenytoin, valproate, Chk and ethosuximide.

Muscle relaxants and anti-Parkinson agents are agents which relax muscles or reduce or eliminate symptoms associated with Parkinson's disease. Examples of such agents include, but are not limited to, mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include, but are not limited to, atropine, scopolamine, oxyphenonium, and papaverine.

Miotics and anti-cholinergics are compounds which cause bronchodilation. Examples include, but are not limited to, echothiophate, pilocarpine, physostigmine salicylate, diisopropylfluorophosphate, epinephrine, neostigmine, carbachol, methacholine, bethanechol, and the like.

Anti-glaucoma compounds include, but are not limited to, betaxalol, pilocarpine, timolol, timolol salts, and combinations of timolol, and/or its salts, with pilocarpine.

Anti-parasitic, -protozoal and -fungals include, but are not limited to, ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include, but are not limited to, alpha-methyldopa and the pivaloyloxyethyl ester of alpha-methyldopa.

Analgesics are substances capable of preventing, reducing, or relieving pain. Examples of analgesics include, but are not limited to, morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include, but are not limited to, aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include, but are not limited to, procaine, lidocain, tetracaine and dibucaine.

Ophthalmics include diagnostic agents such as sodium fluorescein, rose bengal, methacholine, adrenaline, cocaine, and atropine. Ophthalmic surgical additives include, but are not limited to, alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include, but are not limited to, imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include, but are not limited to, phenothiazines, butyrophenones and thioxanthenes.

Anti-emetics are substances which prevent or alleviate nausea or vomiting. An example of such a substance includes, but is not limited to, dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include, but are not limited to, agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include, but are not limited to, dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include, but are not limited to, neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

Uses

Those of ordinary skill in the art will immediately appreciate that the present invention can be utilized in a wide variety of applications to deliver agents into cells. A few particularly preferred applications are discussed in more detail here in order to highlight some of the characteristics and advantages of the inventive systems.

As discussed at length above, the present invention is particularly well adapted for delivery of nucleic acids into cells. As such, the inventive compositions are useful for various applications including gene therapy and antisense regulation. To give but a few examples of particular embodiments of nucleic acid delivery applications of the present invention, inventive compositions can be employed to introduce a gene into specific cells or tissue that will express the protein encoded by that gene and thereby correct a defect caused by a deficiency in that gene in the cells or tissue. Alternatively, inventive compositions can also be used to turn off the function of a specific gene, for example an oncogene in a tumor cell, by delivering antisense messenger RNA into a cell that will bind with the sense messenger RNA so that translation of the message and therefore expression of the protein encoded by that message will not occur.

Inventive compositions can be used in therapeutic gene delivery applications, for example to introduce "suicide genes" into cancer cells that will turn on the cell death pathway. Drug sensitivity genes can also be introduced into tumor cells. For example, cells can be genetically engineered to express prodrug activating enzyme, such as herpes simplex virus thymidine kinase, which phosphorylates ganciclovir creating toxic metabolites that kill tumor cells upon exposure to prodrug.

In the arena of immunotherapy, inventive compositions can be employed in "adoptive immunotherapy" preparations, in which genetically engineered tumor-infiltrating lymphocytes are prepared that express tumor necrosis factor and can be used to treat patients with melanoma. Immunomodulation of tumor cells to invoke an immune response directed toward specific target cell population is yet another area to which this invention can be applied.

Of course, as has already been emphasized, the inventive compositions are not limited in their usefulness to delivery of genes, or even nucleic acids; the compositions can alternatively be used to carry a variety of pharmaceutical compositions. (See Harris, *The Lancet,* 342: 234, 1993).

EXAMPLES

Example 1

Figure 6:
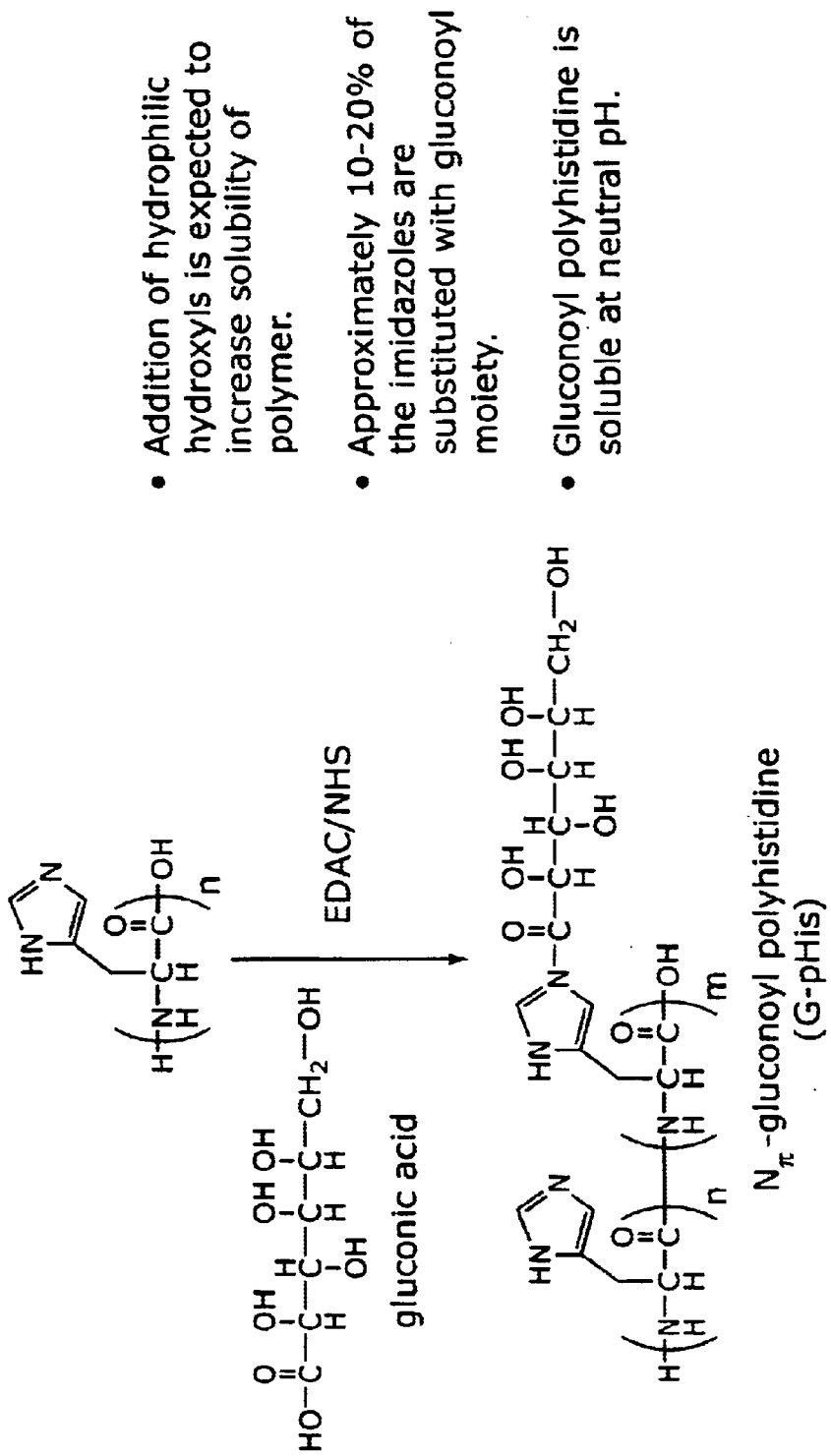
FIG. 6 is a schematic showing derivatization of polyhistidine with gluconic acid that results in improved solubility of gluconoyl-polyhistidine at neutral pH.

Preparation of Gluconic-Acid-Modified Polyhistidine (FIG. 6)

Poly-L-histidine (25 mg, molecular weight range 5,000–15,000, DP=81) was dissolved in 1 mL MES buffer (2-[N-morpholino]ethanesulfonic acid, 25 mM, pH 5.0) to which 17 μL of an aqueous gluconic acid solution (45% w/v) was added and cooled to 4° C. The resulting solution had a final imidazole:gluconic acid mole ratio of 5:1. A solution of EDAC (1-ethyl-3-(3-dimethylaminopropyl)carbodiimide, 776.3 mg, 100 fold molar excess over gluconic acid) and NHS (N-hydroxysuccinimide, 31 mg, NHS:EDAC molar ratio 1:15) was made with 1 mL MES buffer and cooled to 4° C. The EDAC/NHS solution was added to the polyhistidine/gluconic acid solution and allowed to react with stirring at 4° C. for 24 hours. The pH of the reaction was brought to 7.0 with NaOH and centrifuged. The supernatant was placed in a Centricon (Amicon, 3000 molecular weight cutoff) and the solvent changed to distilled water by continued centrifugation and water addition. The resulting solution was lyophilized, redissolved in water and further purified using a water phase PD-10 column. The final product was isolated by lyophilization.

Example 2

Delivery of Nucleic Acid Encoding β-Galactosidase From a Gluconylated-Polyhistidine/Transferrin-Polylysine Composition Preparation of Cell Extract 5×reporter lysis buffer (purchased from Promega, Madison, Wis.) was diluted to 1× with water. The cells were then washed with PBS (2 ml/well in a 6 well dish) and all of the final wash was removed. 400 μL of lysis buffer was then added to each well, and the plate was incubated at 37° C. for 45 minutes. Cell lysis was confirmed by observation of cells under a microscope. The well was then scraped to dislodge the lysed cells and the lysate was transferred to microfuge tubes with a pipet. The lysate was then vortexed and centrifuged at 14,000 rpm for 2 minutes. The supernatant was collected transferred to fresh tubes. The extract was then stored on ice or frozen at −70° C.

ONPG Assay (Spectral Photometric Assay: o-nitrophenyl-β-D-galactopyranoside)

2×assay buffer (200 mM sodium phosphate, pH 7.3; 2 mM magnesium chloride; 100 μM β-mercaptoethanol; 1.33 mg/ml ONPG) was thawed stored on ice. 50 μL of cellular extract was transferred into the wells of a 96 well plate, each sample in triplicate. 50 μL of 2×assay buffer was added to each well and incubated at 37° C. for 30 to 60 minutes. The reaction was then stopped by adding 150 μL 1M NaCO$_3$. The absorbance was then measured at 405 nm on an automatic plate reader.

X-Gal Staining Procedure

Figure 8:
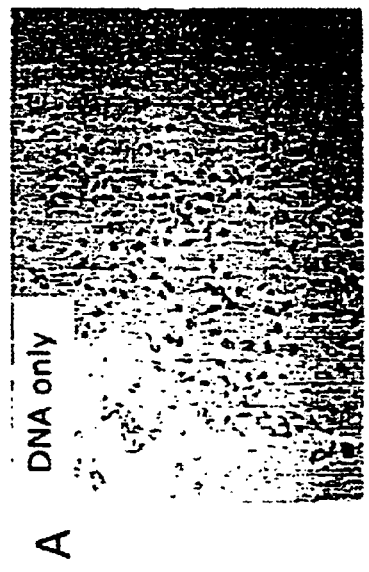
FIG. 8 shows that DNA/gluconoyl-polyhistidine/transferrin-polylysine complexes transfect approximately 10% of COS-7 cells by X-gel staining.
Figure 8:
Figure 8:
Figure 9:
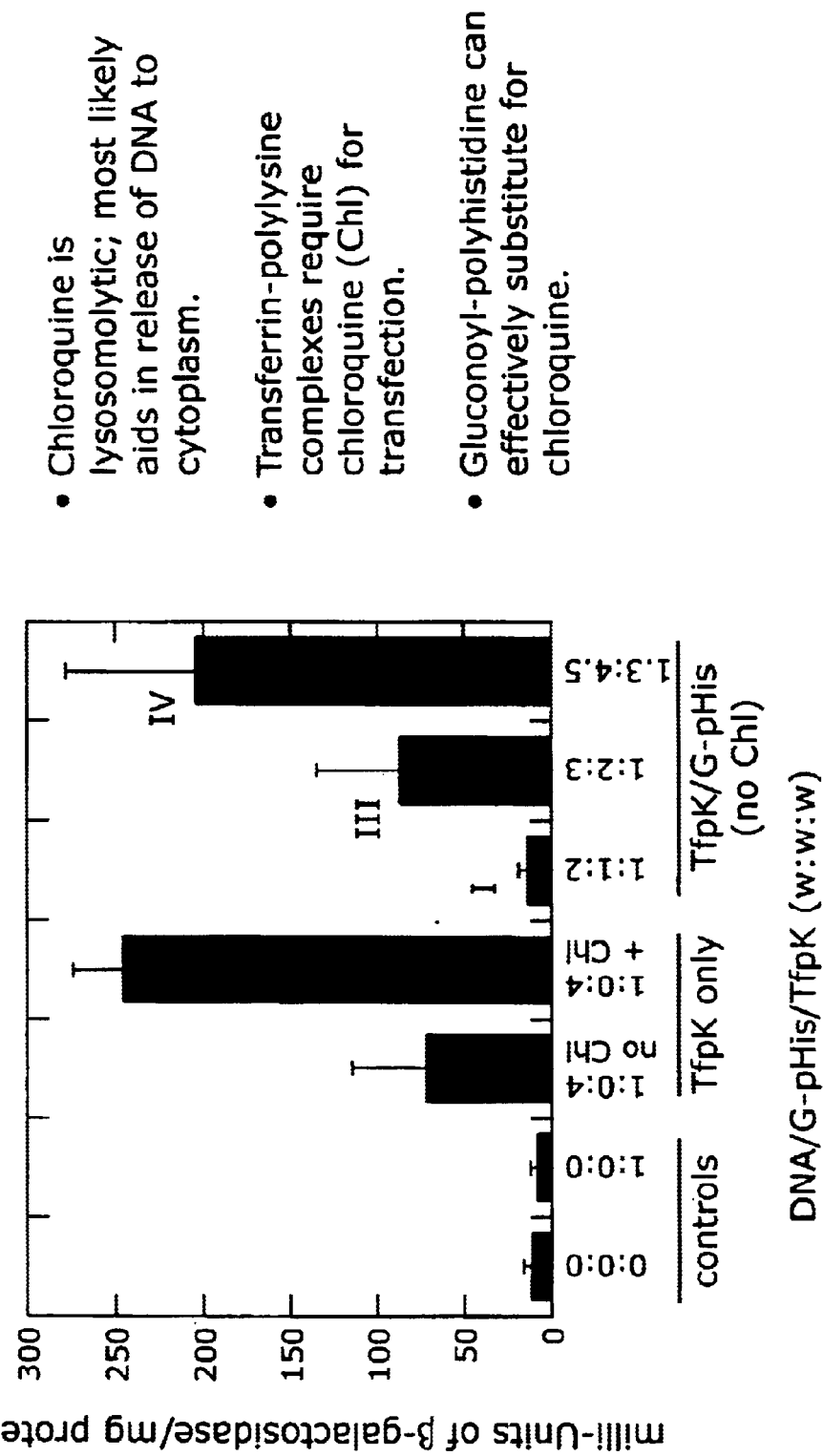
FIG. 9 is a graph that shows the DNA/gluconoyl-polyhistidine/transferrin-polylysine complexes effectively transfect COS-7 cells in culture.
Figure 10:
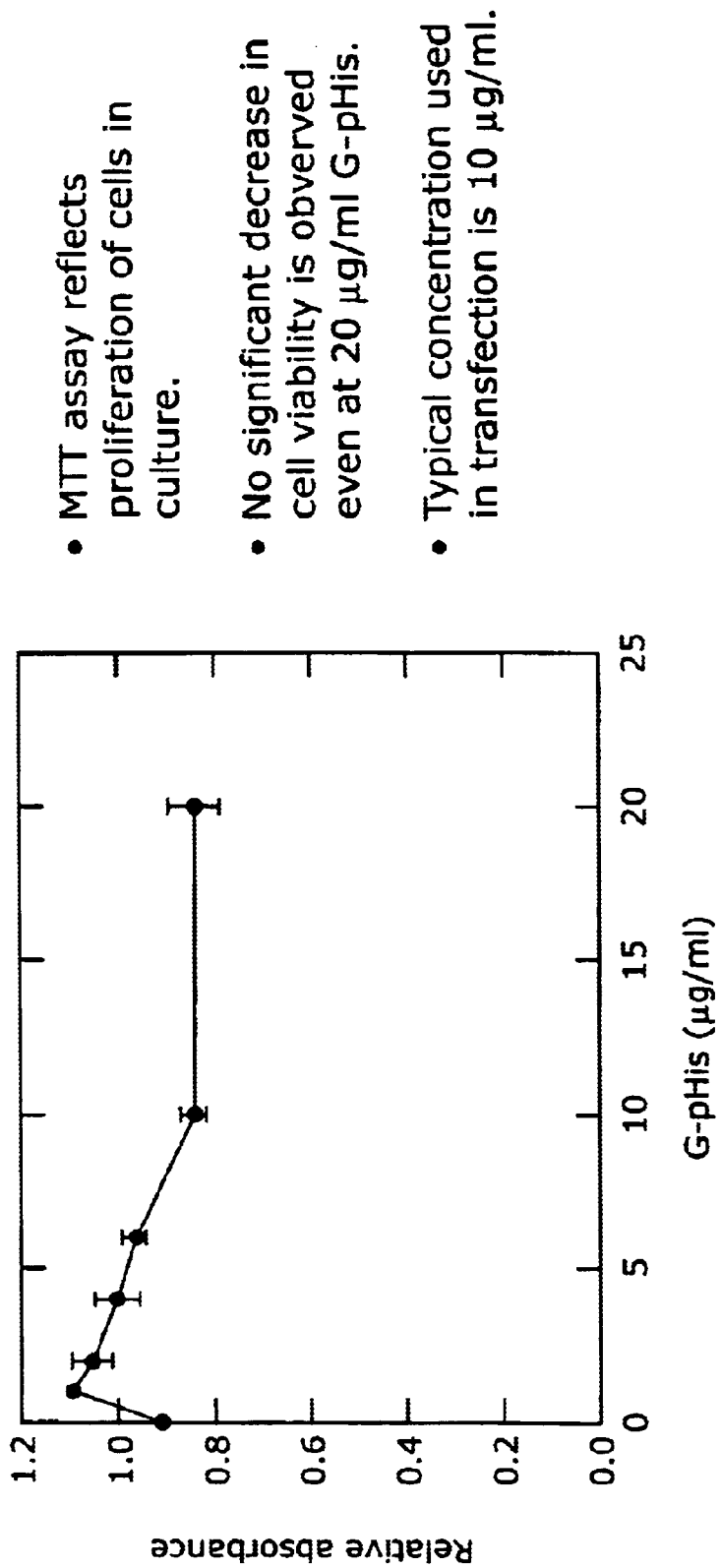
FIG. 10 is a graph showing that gluconoyl-polyhistidine is non-toxic to COS-7 cells in vitro.

The X-gal reagent was prepared according to standard procedures using the following reagents: 3.3 mM K$_4$Fe(CN)$_6$, 3.3 mM K$_3$Fe(CN)$_6$, 1 mM MgCl$_2$, 2 mg/mL X-gal (from 50 mg/mL stock in N,N-dimethylformamide). The cells were washed twice with PBS, 1 mL 0.5% glutaraldehyde was added to each well land the cells were incubated for 15 minutes at room temperature. The glutaraldehyde was removed and the cells were rinsed gently three times with PBS. The final rinse was then completely removed. 1 mL X-gal solution was added to each well and incubated at 37° C. for a time period of at least 2 hours to overnight.

pHis Transfection Protocol 100,000 cells/well were seeded in 6 well tissue culture plates 24 hours prior to transfection. The DNA stock solution was diluted with 30 mM NaOCOCH$_3$, pH 5 to 50 μg/mL. The concentrations of stock solutions for gluconylated polyhistidine and transferrin-polylysine were 230 μg/mL and 300 μg/mL respectively. The concentrations of gluconylated-polyhistidine and transferrin-polylysine were varied, as shown in FIG. 9, in each tube and brought to a final volume of 300 μl with acetate buffer (300 mM sodium acetate, pH 5). The complexes were mixed by adding gluconylated-polyhistidine/transferrin-polylysine solution to DNA such that the final concentration of DNA (pCMV-β-gal) in each well in triplicate was 5 μg. Triplicate wells were provided for each DNA:polyhistidine:transferrin-polylysine ratio tested. The DNA/gluconylated-polyhistidine/transferrin-polylysine transfection solution was incubated for 45 minutes. Meanwhile the cells were washed three times with 2 mL PBS per well. 2.4 mL of Opti-MEM (Gibco, Grand Islands, N.Y.) was added to each of the DNA/gluconylated-polyhistidine/transferrin-polylysine complexes to bring the total volume in the tube to 3.0 mL. 1.0 mL of the complex solution was layered onto each of the triplicate wells such that 5 μg of pCMV-β-gal DNA was delivered to each well and placed in the incubator for 5 hours at which time the transfection medium was removed and replaced with regular growth medium (Dulbecco's modified eagle medium; 10% fetal calf serum, 100 units/mL penicillin, 100 μg/mL streptomycin). Twenty-four hours post-transfection the growth medium was replaced with fresh growth medium. β-galactosidase activity was measured 48 hours post-transfection according to manufacturers instructions (Promega, Madison, Wis.). FIG. 8 shows that the DNA/G-pHis/TfpK complexes transfect approximately 10% of the cells. FIG. 9 shows that gluconyl-polyhistidine can effectively substitute for chloroquine in the transfection of cells. Furthermore, FIG. 10 reveals that G-pHis is non-toxic to cells in vitro and no significant decrease in cell viability is observed.

Ethidium Bromide Exclusion of G-polyhistidine/DNA Complexes

Figure 11:
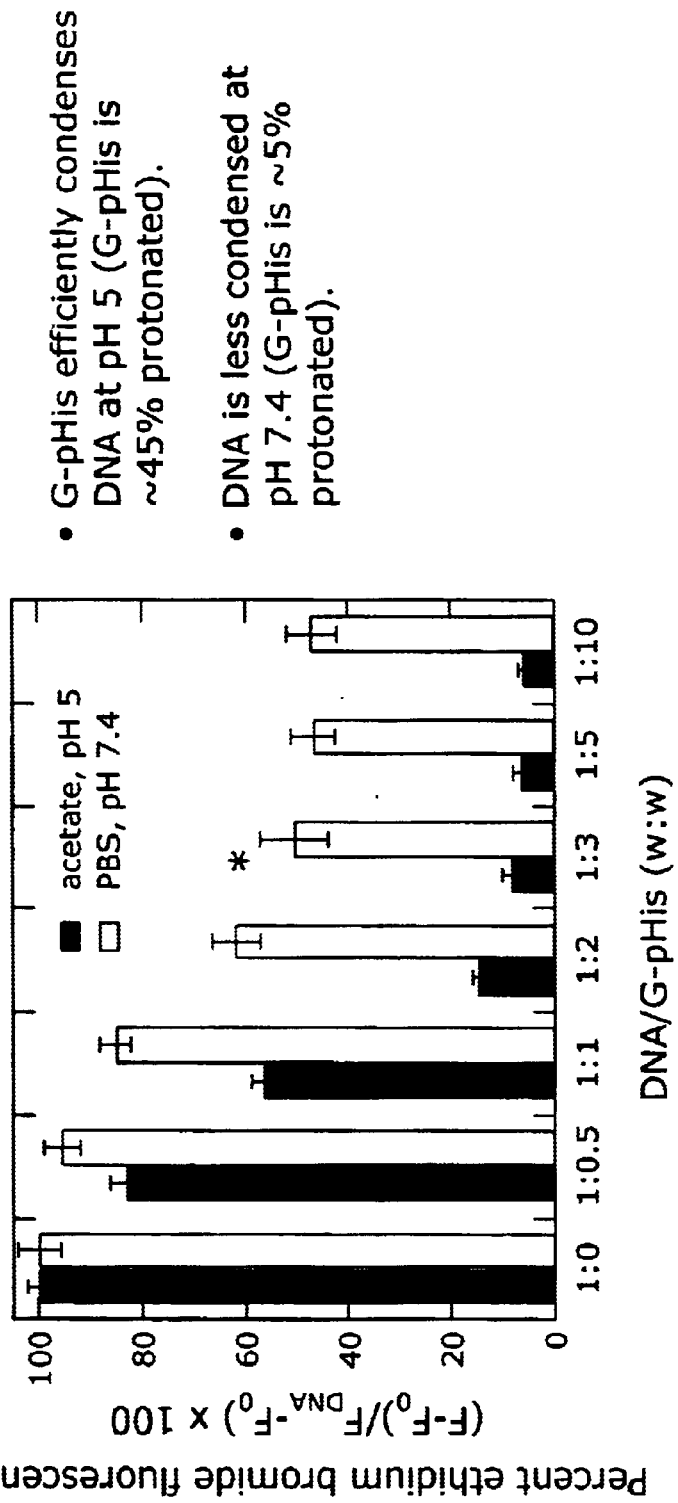
FIG. 11 is a graph that represents data from ethidium bromide exclusion assays showing gluconoyl-polyhistidine condenses plasmid DNA efficiently at pH 5, but plasmid DNA is less condensed at pH 7.4.
Figure 12:
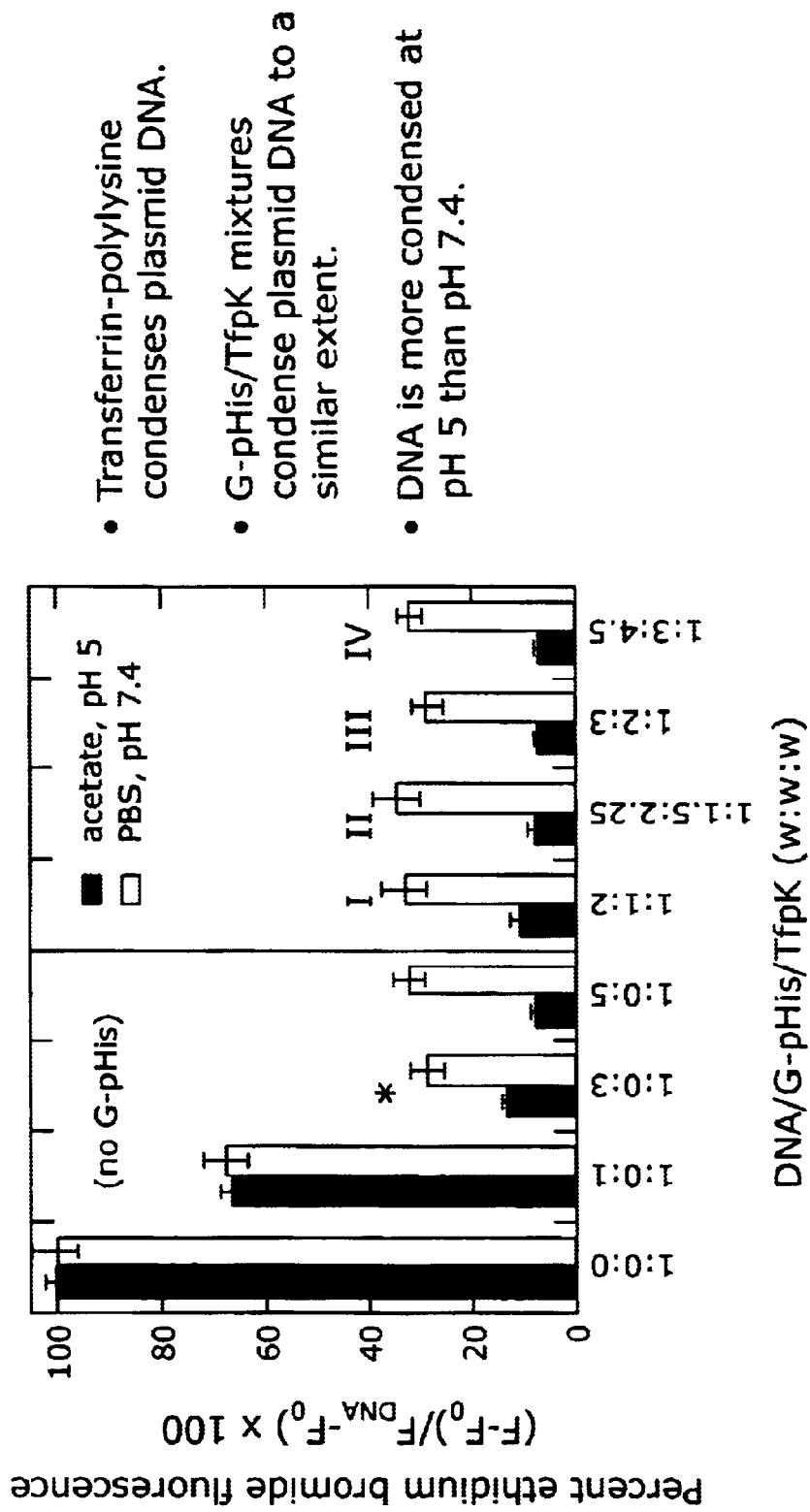
FIG. 12 is a graph showing ethidium exclusion by DNA/transferrin-polylysine and DNA/gluconoyl-polyhistidine/transferrin-polylysine complexes.

The final DNA concentration is 1 μM in base pairs. The ethidium bromide molecule:DNA base pair ratio is 1:1. 2.11 μg of pCMV-β-gal DNA was added to 100 μL of 30 mM NaOCOCH$_3$ (pH 5). A range of 0–20.1 μg gluconylated-polyhistidine was made up in a volume of 100 μL with 30 mM NaOCOCH$_3$ (pH 5). The gluconylated polyhistidine was added to the DNA solution and incubated 30 minutes at room temperature. 30 mM NaOCOCH$_3$ (pH 5) and PBS (pH 7.4) buffers were each pre-filtered through 0.22 um syringe filters. Each DNA/gluconylated-polyhistidine (w/w) was diluted 1 to 2.5 mL with NaOCOCH₃ (pH 5) buffer and 1 to 2.5 mL with PBS (pH 7.4). 11.8 µL of 100 µg/mL ethidium bromide was added to each sample in triplicate. 0.8 ml of the DNA/gluconylated-polyhistidine complex in either 30 mM NaOCOCH₃ (pH 5) or PBS (pH 7.4) was loaded to a photon correlation spectrometer (Brookline Instruments Corp.) to measure complex size by light scattering. FIG. 11 demonstrates the G-pHis efficiently condenses DNA at pH 5. This procedure was also repeated for the DNA/G-pHis/TfpK complex and the results are shown in FIG. 12.

Example 3

Assaying DNA Complexation by Cationic Polymers

Figure 13:
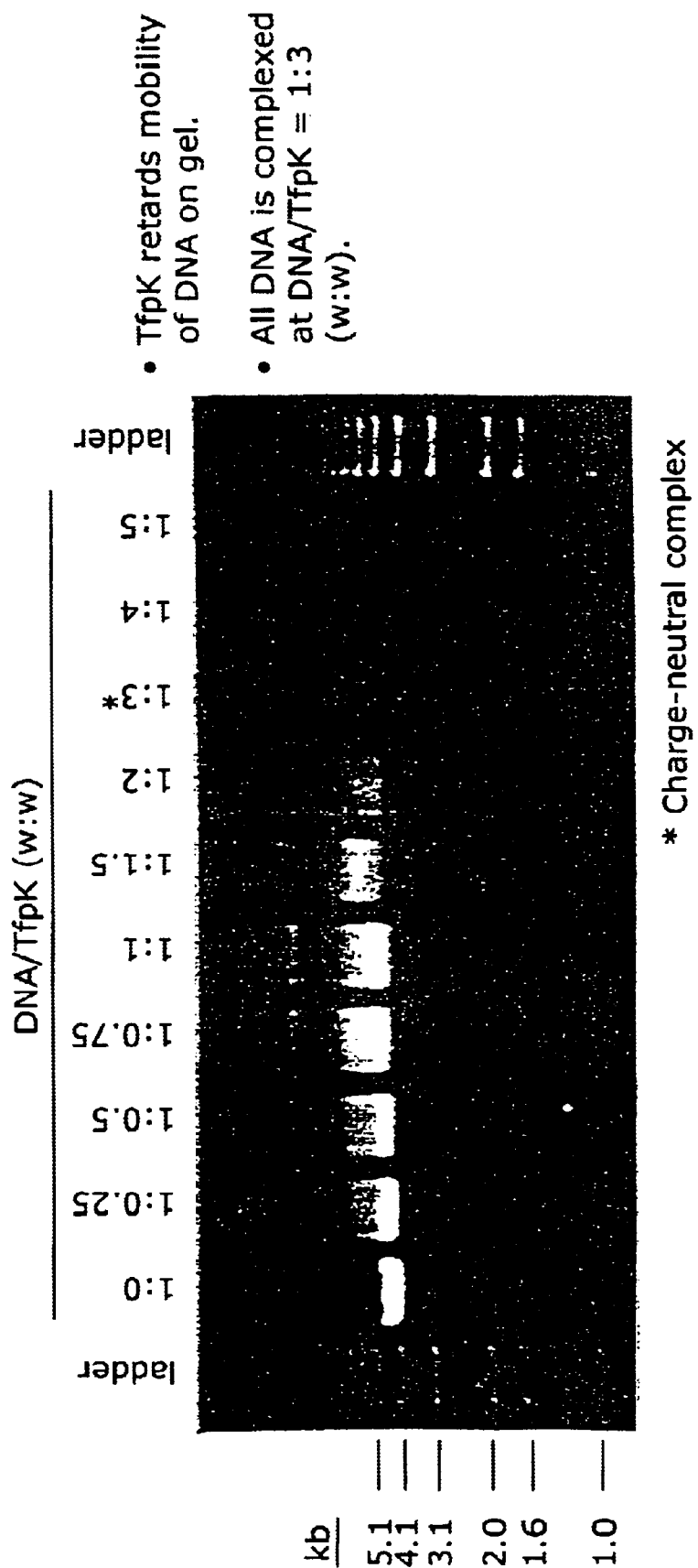
FIG. 13 presents gel electrophoresis of DNA/transferrin-polylysine mixtures that reveals complex formation.
Figure 14:
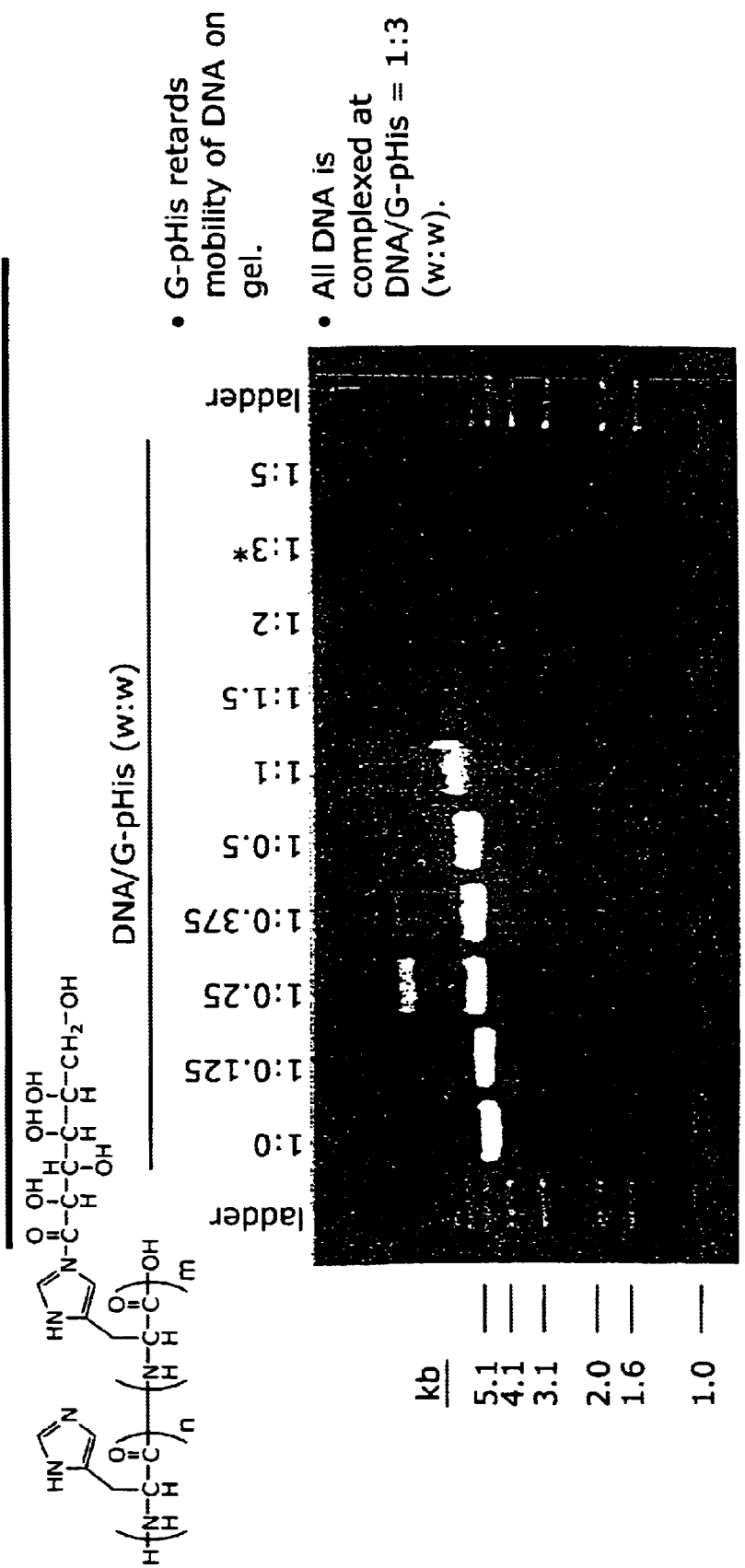
FIG. 14 presents gel electrophoresis of DNA/gluconoyl-polyhistidine mixtures that reveals complex formation.
Figure 15:
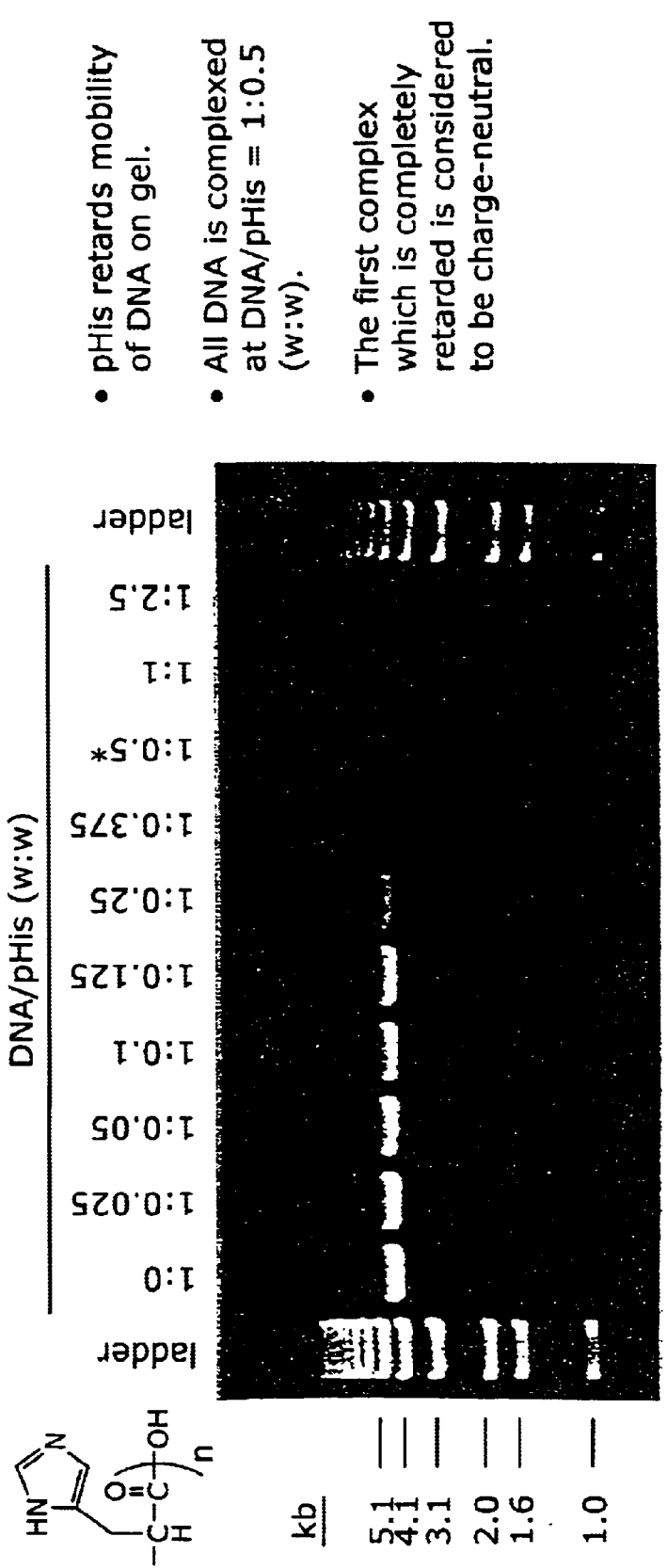
FIG. 15 presents gel electrophoresis of DNA/polyhistidine mixtures revealing complex formation.

The ability of the packaging agent to bind DNA can be assessed by monitoring complex formation with DNA using gel electrophoresis. The mobility of DNA on the gel will be retarded by complex formation, and the absence of any mobility of DNA on the gel suggests the complexation of all of the DNA. Preferably, complexation of DNA and the cationic polymer occurs as a ratio of 1:1 DNA/cationic polymer, and most preferably at a ratio of 1:3 DNA/cationic polymer as shown in FIGS. 13 and 14 for DNA transferrin-polylysine and DNA/G-pHis mixtures. FIG. 15 depicts the gel electrophoresis of DNA/p-His mixtures and shows complexation at a weight:weight ratio of 1:0.5 DNA/p-His. Condensing of plasmid DNA can also be monitored by observing the ethidium bromide exclusion. For example, if gluconylated polyhistidine is used as the cationic polymer, the gluconylated polyhistidine efficiently condenses DNA at pH 5 where the gluconylated polyhistidine is ~45% protonated. DNA is not condensed as effectively, however, at pH 7.4 where gluconylated polyhistidine is ~5% protonated, as shown in FIG. 11.

Other Embodiments

Those of ordinary skill in the art will appreciate that the foregoing has been a description of certain preferred embodiments of the present invention. This description is not intended to limit the spirit or scope of the present invention, as embodied in the following claims.

We claim:

1. A biocompatible composition comprising:
a delivery agent, characterized by an ability to bind to a nucleic acid and mediate import into endosomes, wherein the delivery agent is selected from the group consisting of polylysine, polyhistidine, lysine, histidine, and combinations thereof;
the nucleic acid, wherein the delivery agent forms a non-covalent complex with a nucleic acid having a nucleic acid to delivery agent weight:weight ratio in the range of 1:3 to 1:10; and
an imidazole-containing endosomal lysing agent, wherein the endosomal lysing agent is free of chloroquine, fusogenic peptides, inactivated adenoviruses, and polyethyleneimine; and wherein the endosomal lysing agent is selected from the group consisting of histidine, histamine, vinylimidazole, polymers thereof, and any combinations of histidine, histamine, vinylimidazole, and polymers thereof.

2. A biocompatible composition comprising:
a delivery agent, characterized by an ability to bind to a nucleic acid and mediate import into endosomes, wherein the delivery agent is selected from the group consisting of polylysine, polyhistidine, lysine, histidine, and combinations thereof;
the nucleic acid, wherein the delivery agent forms a non-covalent complex with a nucleic acid having a nucleic acid to delivery agent weight:weight ratio of 1 to at least 3; and
an imidazole-containing endosomal lysing agent, wherein the endosomal lysing agent is free of chloroquine, fusogenic peptides, inactivated adenoviruses, and polyethyleneimine; and wherein the endosomal lysing agent is selected from the group consisting of histidine, histamine, vinylimidazole, polymers thereof, and any combinations of histidine, histamine, vinylimidazole, and polymers thereof.

3. A biocompatible composition comprising:
a delivery agent, characterized by an ability to bind to a nucleic acid and mediate import into endosomes, wherein the delivery agent is selected from the group consisting of polylysine, polyhistidine, lysine, histidine, and combinations thereof;
the nucleic acid, wherein the delivery agent forms a non-covalent complex with the nucleic acid; and
an imidazole-containing endosomal lysing agent, wherein the endosomal lysing agent is present at a nucleic acid to endosomal lysing agent weight:weight ratio in the range of 1:1.5 to 1:10; wherein the endosomal lysing agent is free of chloroquine, fusogenic peptides, inactivated adenoviruses, and polyethyleneimine; and wherein the endosomal lysing agent is selected from the group consisting of histidine, histamine, vinylimidazole, polymers thereof, and any combinations of histidine, histamine, vinylimidazole, and polymers thereof.

4. A biocompatible composition comprising:
a delivery agent, characterized by an ability to bind to a nucleic acid and mediate import into endosomes, wherein the delivery agent is selected from the group consisting of polylysine, polyhistidine, lysine, histidine, and combinations thereof;
the nucleic acid, wherein the delivery agent forms a non-covalent complex with the nucleic acid; and
an imidazole-containing endosomal lysing agent, wherein the endosomal lysing agent is present at a nucleic acid to endosomal lysing agent weight:weight ratio in the range of 1 to at least 1.5; wherein the endosomal lysing agent is free of chloroquine, fusogenic peptides, inactivated adenoviruses, and polyethyleneimine; and wherein the endosomal lysing agent is selected from the group consisting of histidine, histamine, vinylimidazole, polymers thereof, and any combinations of histidine, histamine, vinylimidazole, and polymers thereof.

5. The composition of claim 1, 2, 3, or 4, wherein the delivery agent is polylysine.

6. The composition of claim 1, 2, 3, or 4, wherein the delivery agent condenses the nucleic acid.

7. The composition of claim 1, 2, 3, or 4, wherein the delivery agent condenses the nucleic acid to a size less than 150 nm.

8. The composition of claims 1, 2, 3, or 4, wherein one or both of the delivery agent and the endosomal lysing agent is further functionalized with a hydrophilic moiety.

9. The composition of claim 8, wherein the hydrophilic moiety is selected from the group consisting of gluconic acid, carbohydrates, nucleic acids, and amino acids.

10. The composition of claim 1, 2, 3, or 4, wherein one or both of the delivery agent and the endosomal lysing agent is covalently linked to a targeting ligand.

11. The composition of claim 10, wherein the targeting ligand is selected from the group consisting of transferrin, low-density lipoprotein (LDL), asiaglycoproteins, gp120 envelope protein of the human immunodeficiency virus (HIV), diptheria toxin, antibodies, and carbohydrates.

12. The composition of claim 1, 2, 3, or 4, wherein the endosomal lysing agent is polyhistidine.

13. The composition of claim 1, 2, 3, or 4, wherein the endosomal lysing agent comprises a gluconic-acid-modified polyhistidine.

14. The composition of claim 1, 2, 3, or 4, wherein the endosomal lysing agent comprises a polymeric lysing agent.

15. The composition of claim 14, wherein the polymeric lysing agent is in a form selected from the group consisting of:
    mixed polymers;
    linear co-polymers;
    branched co-polymers; and
    dendrimer branched co-polymers.

16. The composition of claim 1, 2, 3, or 4, wherein the endosomal lysing agent is polyhistidine, and the delivery agent is polylysine.

17. The composition of claim 1, 2, 3, or 4, wherein the delivery agent and the endosomal lysing agent comprise a same material.

18. The composition of claim 1, 2, 3, or 4, wherein the delivery agent and the endosomal lysing agent comprise two or more materials.

19. The composition of claim 1, 2, 3, or 4, wherein the endosomal lysing agent is selected from the group consisting of:
    polyhistidine;
    polyhistidine and polylysine;
    lysine and polyhistidine;
    histidine and polylysine;
    lysine and histidine; and
    any combinations thereof.

20. The composition of claim 19, wherein the endosomal lysing agent is in a form selected from the group consisting of:
    mixed polymers;
    linear co-polymers;
    branched co-polymers; and
    dendrimer branched co-polymers.

21. A method of lysing an endosome, the method comprising steps of:
    providing a composition for endosomal uptake into a cell, the composition comprising:
        a nucleic acid; and
        a delivery agent, wherein the delivery agent forms a non-covalent complex with the nucleic acid having a nucleic acid to delivery agent weight:weight ratio of 1 to at least 3, and
        wherein the delivery agent is selected from the group consisting of polylysine, polyhistidine, lysine, histidine, and combinations thereof; and
    contacting the composition with the cell in the presence of an imidazole-containing endosomal lysing agent, wherein the endosomal lysing agent is selected from the group consisting of histidine, histamine, vinylimidazole, polymers thereof, and any combinations of histidine, histamine, vinylimidazole, and polymers thereof; and
    wherein the endosomal lysing agent is free of chloroquine, fusogenic peptides, inactivated adenoviruses, and polyethyleneimine.

22. A method of lysing an endosome, the method comprising steps of:
    providing a composition for endosomal uptake into a cell comprising:
        a nucleic acid; and
        a delivery agent, wherein the delivery agent forms a non-covalent complex with the nucleic acid having a nucleic acid to delivery agent weight:weight ratio in the range of 1:3 to 1:10, and
        wherein the delivery agent is selected from the group consisting of polylysine, polyhistidine, lysine, histidine, and combinations thereof; and
    contacting the composition with the cell in the presence of an endosomal lysing agent, wherein the endosomal lysing agent is selected from the group consisting of histidine, histamine, vinylimidazole, polymers thereof, and any combinations of histidine, histamine, vinylimidazole, and polymers thereof; and
    wherein the endosomal lysing agent is free of chloroquine, fusogenic peptides, inactivated adenoviruses, and polyethyleneimine.

23. The method of claim 21 or 22, wherein the endosomal lysing agent is polyhistidine.

24. The method of claim 21 or 22, wherein the endosomal lysing agent is a gluconic-acid-modified polyhistidine.

25. The method of claim 21 or 22, wherein the endosomal lysing agent is a polymeric lysing agent.

26. The method of claim 25, wherein the polymeric lysing agent is in a form selected from the group consisting of:
    mixed polymers;
    linear co-polymers;
    branched co-polymers; and
    dendrimer branched co-polymers.

27. The method of claim 21 or 22, wherein the endosomal lysing agent is functionalized with one or more hydrophilic groups.

28. The method of claim 27, wherein said one or more hydrophilic groups is selected from the group consisting of gluconic acid, carbohydrates, nucleic acids, and amino acids.

29. The method of claim 21 or 22, wherein the endosomal lysing agent further comprises a targeting agent selected from the group consisting of low density lipoproteins, transferrin, asialycoproteins, gp120 envelope protein of human immunodeficiency virus, antibodies, and carbohydrates.

30. The method of claim 21 or 22, wherein the endosomal lysing agent is selected from the groups consisting of:
    polyhistidine;
    polyhistidine and polylysine;
    lysine and polyhistidine;
    histidine and polylysine;
    lysine and polyhistidine; and
    and combinations thereof.

31. The method of claim 30, wherein the endosomal lysing agent is in a form selected from the group consisting of:

mixed polymers;

linear co-polymers;

branched co-polymers; and dendrimer branched co-polymers.

32. The method of claim 21 or 22, wherein the delivery agent is polylysine; and the endosomal lysing agent is polyhistidine.

33. The method of claim 21 or 22, wherein the delivery agent condenses the nucleic acid.

34. The method of claim 21 or 22, wherein the delivery agent condenses the nucleic acid to a size less than 150 nm.

35. The method of claim 21 or 22, wherein the delivery agent is polylysine.

36. The method of claim 21 or 22, wherein one or both of the delivery agent and the endosomal lysing agent are functionalized with a hydrophilic moiety.

37. The method of claim 36, wherein said hydrophilic moiety is selected from the group consisting of gluconic acid, carbohydrates, nucleic acids, and amino acids.

38. The method of claim 21 or 22, wherein one or both of the delivery agent and the endosomal lysing agent are covalently linked to a targeting ligand.

39. The method of claim 38, wherein the targeting ligand is selected from the group consisting of transferrin, low-density lipotprotein (LDL), asiaglycoproteins, gp120 envelope protein of human immunodeficiency virus (HIV), diptheria toxin, antibodies, and carbohydrates.

* * * * *

UNITED STATES PATENT AND TRADEMARK OFFICE
CERTIFICATE OF CORRECTION

| | | |
|---|---|---|
| PATENT NO. | : 6,692,911 B2 | Page 1 of 1 |
| APPLICATION NO. | : 09/251783 | |
| DATED | : February 17, 2004 | |
| INVENTOR(S) | : Pack et al. | |

It is certified that error appears in the above-identified patent and that said Letters Patent is hereby corrected as shown below:

Please insert the following at column 1, line 2:

-- Sponsorship Information
This invention was made with government support under Grant Number R01 GM026698 awarded by the National Institutes of Health. The government has certain rights in the invention. --

Signed and Sealed this
Fourteenth Day of February, 2012

David J. Kappos
*Director of the United States Patent and Trademark Office*